(12) United States Patent
Mack

(10) Patent No.: US 7,805,263 B2
(45) Date of Patent: Sep. 28, 2010

(54) WIRELESS BATTERY STATUS MANAGEMENT FOR MEDICAL DEVICES

(75) Inventor: Hanns-Ingo Mack, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 602 days.

(21) Appl. No.: 11/718,550

(22) PCT Filed: Nov. 4, 2005

(86) PCT No.: PCT/IB2005/053609

§ 371 (c)(1),
(2), (4) Date: May 3, 2007

(87) PCT Pub. No.: WO2006/048838

PCT Pub. Date: May 11, 2006

(65) Prior Publication Data

US 2008/0312852 A1 Dec. 18, 2008

Related U.S. Application Data

(60) Provisional application No. 60/625,890, filed on Nov. 8, 2004.

(51) Int. Cl.
*H05G 1/08* (2006.01)
*G06F 11/30* (2006.01)

(52) U.S. Cl. .............. 702/63; 702/60; 702/61; 702/62; 702/188; 340/636.19; 340/636.1; 340/286.07; 378/102; 320/132; 320/134; 320/136

(58) Field of Classification Search ............ 702/63, 702/60, 61, 62, 188
See application file for complete search history.

(56) References Cited

U.S. PATENT DOCUMENTS

| | | | |
|---|---|---|---|
| 4,324,251 A | 4/1982 | Mann | |
| 5,193,538 A | 3/1993 | Ekwall | |
| 6,084,523 A * | 7/2000 | Gelnovatch et al. | 340/636.1 |
| 6,108,579 A | 8/2000 | Snell et al. | |
| 6,449,726 B1 * | 9/2002 | Smith | 713/340 |
| 6,760,625 B1 * | 7/2004 | Kroll | 607/29 |
| 2002/0128051 A1 | 9/2002 | Liebenow | |
| 2003/0083011 A1 * | 5/2003 | Haller et al. | 455/41 |
| 2003/0114899 A1 * | 6/2003 | Woods et al. | 607/60 |
| 2004/0073127 A1 * | 4/2004 | Istvan et al. | 600/513 |
| 2008/0183229 A1 * | 7/2008 | Neumiller et al. | 607/5 |

* cited by examiner

Primary Examiner—Hal D Wachsman (57) ABSTRACT

In a wireless battery operated medical component (10), a battery life monitor, particularly a voltage monitor (16), takes voltage readings of a battery (12) to assess charge level as the battery (12) drains. The monitored charge level and medical data are transmitted (20) to a receiver (22) associated with a remote host unit (24). The host unit includes historical and typical battery level information and estimates remaining life of the battery (12). Battery life and medical information are displayed on a user interface (42). Typical battery operated medical components include EKG sensors, pulse sensors, blood oxygen sensors, blood measure sensors, brain wave sensors, temperature sensors, perfusion pumps, IV drip controllers, patient identification tags or wrist bands, pacemakers, respirators, x-ray detectors, and an MRI coils.

9 Claims, 6 Drawing Sheets

WIRELESS BATTERY STATUS MANAGEMENT FOR MEDICAL DEVICES

CROSS REFERENCE TO RELATED APPLICATIONS

This application claims priority under 35 U.S.C. §371 from International PCT application ser. No. PCT/IB2005/053609 filed Nov. 4, 2005 which claims the benefit of U.S. provisional application ser. No. 60/625,890 filed Nov. 8, 2004, which is incorporated herein by reference.

The present invention relates to wireless patient devices. It finds particular application with physiological monitoring devices that are connected to the patient and communicate wirelessly to each other and a central unit. However, the invention is also applicable to dosing devices, such as perfusion pumps, which are wirelessly controlled, and the like.

BACKGROUND

Traditionally, patient monitors, such as an EKG sensor, pulse sensor, blood oxygen sensor, and the like are each connected with its control unit by a cable. This maze of cables is inconvenient to set up and uncomfortable for the patient. Moreover, moving the patient typically requires disconnecting the cables and reconnecting them after the move. In addition to the inconvenience, the patient is left unmonitored during the move.

In an effort to eliminate the cables, wireless battery powered sensor devices have been proposed. However, when monitoring patients' vital signs, or dosing a critical medication, a dead battery can be more than inconvenient; it can be life threatening.

Often, a battery operated component is equipped with a sensor that measures the battery's current charge level. Some provide a simple green light for a strong charge and a red light for a weak charge, i.e., the battery is about to run out. Others provide a gauge which indicates the remaining portion of battery life. Battery life gauges merely indicate a level of charge—not when a battery will run out. Nominally similar batteries will hold different amounts of maximum charge or discharge at different rates. As batteries age, they tend to have progressively shorter lives In a hospital, one patient may have several monitors, perhaps half a dozen or more. With hundreds of patients being monitored, checking the battery status indicators of all the monitors is a logistical nightmare. Thus, on-device battery level monitors do not assure freedom from battery problems in life threatening situations.

Due to these and other problems, system designers have been reluctant to replace standard wired devices with wireless devices when the devices are more critical in nature. If a battery should fail at an inopportune moment, consequences could range from mere annoyances to potentially life threatening situations and malpractice/product liability lawsuits. Nonetheless, some critical devices are equipped with batteries, such as portable respirators and intravenous fluid pumps. Additionally, sometimes non-critical devices are used in a critical situation, such as diagnostic imaging in conjunction with a trauma victim. In an extreme case, if one of these devices should fail due to insufficient battery power, the results could be catastrophic.

SUMMARY

The present application contemplates a new and improved battery monitoring system for use in conjunction with units with wireless communication, which overcomes the above-referenced problems and others.

In accordance with one aspect of the present invention, a medical system is provided. A wireless medical component includes a functional component which performs a medical procedure, a wireless power supply which powers the functional component, a charge level monitor that monitors a charge level of the power supply, and a transmitter that wirelessly transmits signals from the functional component and the charge level monitor. The medical system also includes a host device connected with a receiver that receives the transmitted signals from the wireless medical component. The host device includes a medical function signal interpreting means for interpreting the signals received from the functional component and a battery analysis means for determining an estimated remaining operating time of the wireless medical component.

In accordance with another aspect of the present invention, a method of monitoring the life of a battery of a wireless medical component is provided. A medical procedure is performed with a functional component, while a charge level of a power supply that powers the functional component is monitored with a charge level monitor. Signals carrying information from the functional component and the power level monitor are wirelessly transmitted from the component and received with a host device. The signals received from the functional component are interpreted, and an estimated remaining operating time of the wireless medical component is determined from the received signals.

One advantage of the present invention is better reliability for systems with battery operated components.

Another advantage is better battery management of several similar devices.

Another advantage is increased reliability for battery operated components.

Another advantage lies in increased safety of battery operated critical systems.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

DESCRIPTION

Figure 1:
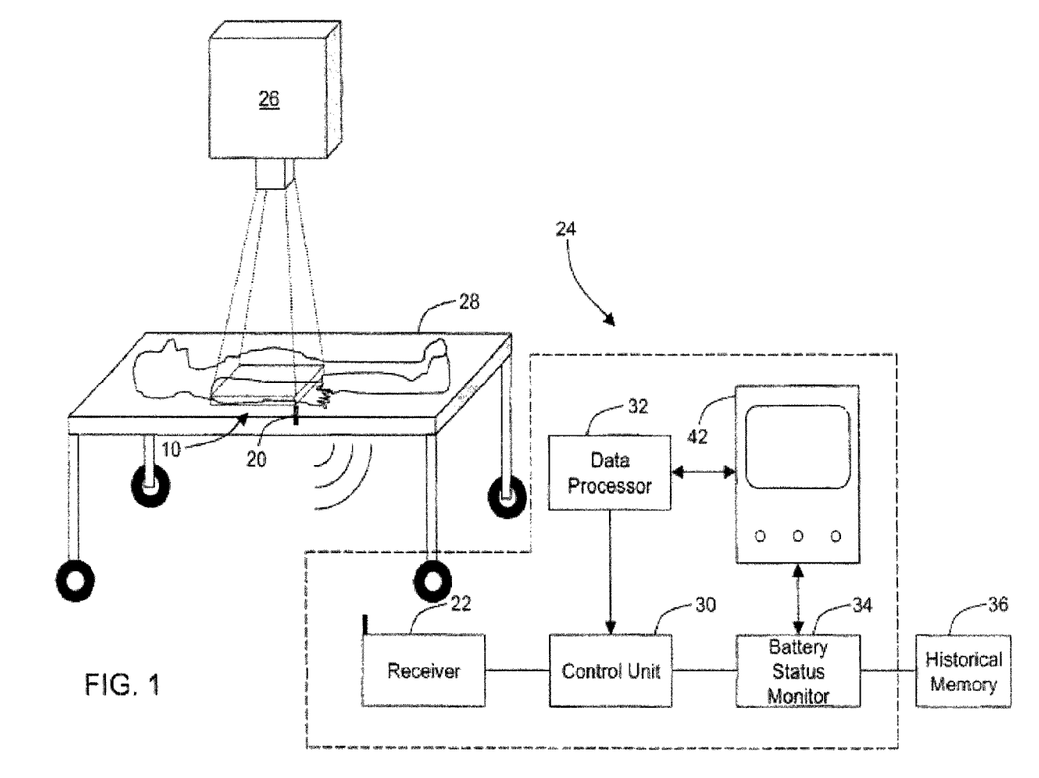
FIG. 1 is a diagrammatic illustration of a preferred implementation of a wireless medical component and battery monitoring system.
Figure 2:
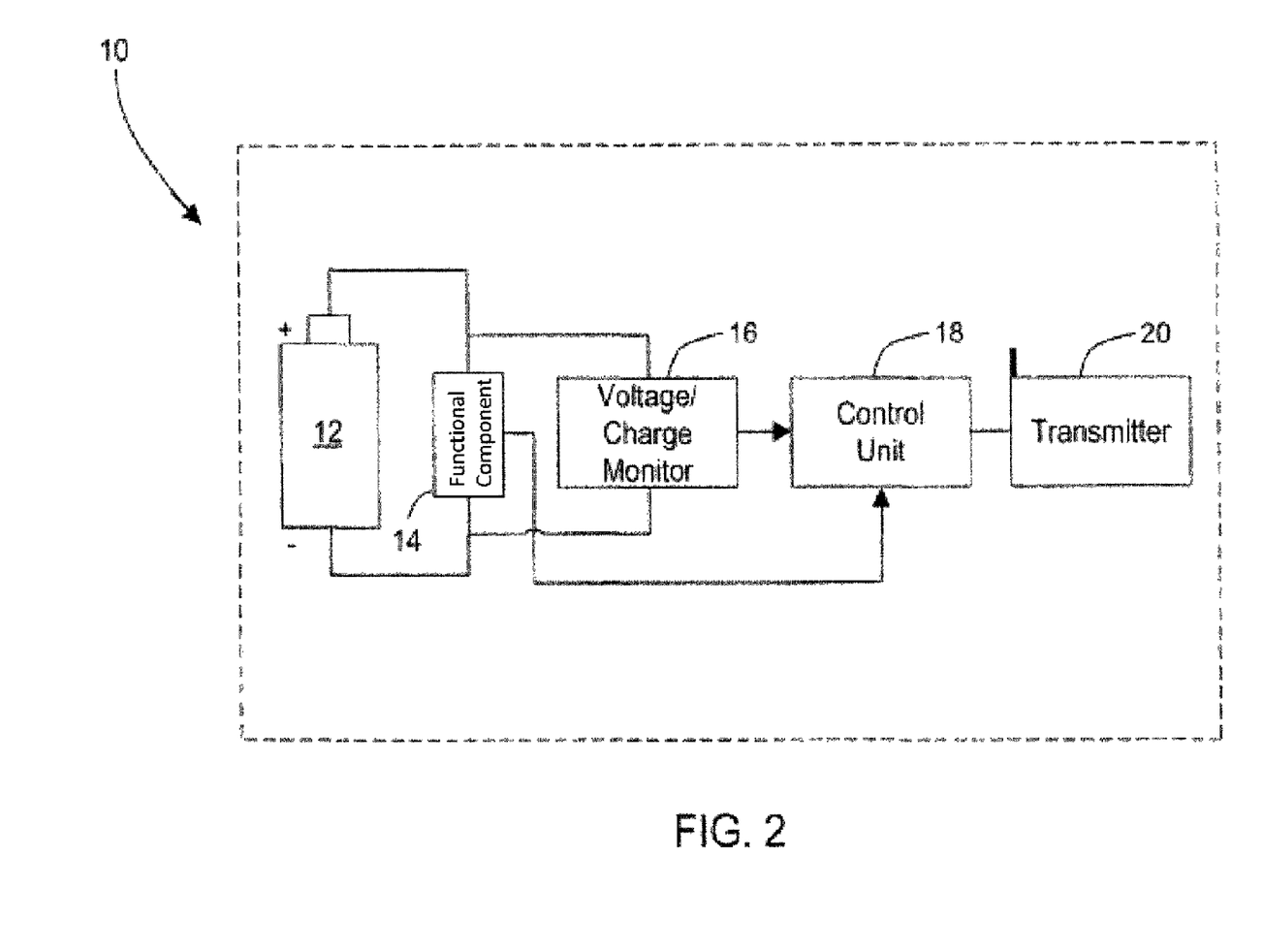
FIG. 2 is a more detailed representation of the wireless medical component of FIG. 1.

With reference to FIG. 1, a wireless medical component 10 is used in a clinical fashion. Being wireless, the component 10 has the advantage of mobility, and is not anchored to a certain room or spot. As the component 10 still uses electrical power to perform its function or communicate, it has a battery or other portable power supply. With reference to FIG. 2, the component 10 is shown in more detail. The component 10 is powered by a rechargeable power supply or battery 12. Preferably, the battery 12 is rechargeable, such that a user can plug the component 10 in to a docking station to recharge it when not in use. It is to be understood that conventional non-rechargeable batteries are also contemplated, though they are slightly less convenient. The battery 12 provides power to a battery powered medical component functional element 14, such as a battery powered medical component EKG sensor, a battery powered medical component pulse sensor, a battery powered medical component blood oxygen sensor, a battery powered medical component blood measure sensor, a battery powered medical component brain wave sensor, a battery powered medical component temperature sensor, a battery powered medical component perfusion pump, a battery powered medical component IV drip controller, a battery powered medical component patient identification tag or wrist band, a battery powered medical component pacemaker, a battery powered medical component respirator, a battery powered medical component x-ray detector, a battery powered medical component MRI coil, or the like. Typically, the battery powered functional medical components associated with each patient communicate wirelessly with each other and form an ad hoc network.

Because these components 10 are battery powered, it is advantageous to be aware of the remaining battery life so the component does not fail on the user at an inopportune moment. To that end, the component 10 also includes a battery level or charge level monitor, e.g. a voltage monitor 16 that continuously monitors the voltage output of the battery 12. In the preferred embodiment, the voltage monitor only takes voltage readings, and does not interpret the data it collects. On-board interpretation of the data is contemplated and would be more costly in that it might include extra circuit components, such as an extra dedicated microprocessor which would increase monetary cost and shorten the battery life. A microprocessing control unit 18 processes the monitored function data, a device ID, possibly a network or patient identifier, information received from other components, and the like along with the battery level data for wireless transfer. With reference to FIG. 1 and continuing reference to FIG. 2, a wireless transmitter 20 transmits the data to a receiver 22 connected with a host device 24. The wireless transmitter is preferably a low power, short range transmitter, such as infrared, Bluetooth, ZigBee, low strength radio frequency (RF) waves, or the like. Of course, longer range modalities can be used, but it is preferred that a short range, low strength transmission is used. Short range transmissions will meet most, if not all clinical needs. With low power transmissions, the receiver 22 is place close to the patient. The host device 24 is connected with the receiver by a transmission cable, a wireless LAN, or the like. Alternately, the host device 24 is dedicated to a specific component and is mounted with the receiver 22. For example, the recharging station, the receiver 22 and the host device 24 can be mounted to a mobile cart. Rather than continuous transmissions, the control unit 18 can keep a rotating log of recent measurements and transmit all the measurements from recent history periodically, when polled by the host device 24, or the like.

With reference to FIG. 1, in an exemplary x-ray detector embodiment, a portable x-ray source 26 transmits diagnostic x-rays through a subject located on a support surface 28, typically the patient's bed. The patient would be x-rayed in their bed and the detector 10 placed between them and the bed. Alternately, the detector 10 can be used in conjunction with a stationary x-ray unit 26. The patients would be transported to a dedicated x-ray room. Once again, the component 10 is depicted in FIG. 1 as an x-ray detector, but the present application is available to myriad other battery powered medical devices. The transmitter 20 of the component 10 regularly transmits packets of information to the host device 24 that contain the voltage readings, the image data, and the like. Additionally, the data packets preferably contain a component identification, that may include the type of battery 12 that powers the component. The receiver 22, preferably connected to the host device 24 via an Ethernet LAN connection, receives the packets of information. In one embodiment, the transmitter transmits packets of data after each image is taken and battery information periodically in between. A reasonable balance is desired between battery conservation and constant battery monitoring. In the preferred embodiment, the transmitter 20 transmits battery information every five minutes, but this length of time can be shorter or longer, depending on the application.

Once the receiver 22 receives the data packet containing the voltage data from the component 10, the data packet is demodulated by a host control unit 30, converting the wireless signal back into voltage data and diagnostic data. The diagnostic data is sent to a diagnostic data processor 32, such as an, image processor in the x-ray imaging embodiment and a battery status monitor 34. Although preferably software routines of a common processor, these functions are illustrated separately or simplicity of illustration. The receiver 22 and the host control unit 30, and the data processor 32 can collectively be referred to as a subsystem. The subsystem preferably performs an automatic picture or graphic processing operation with no user input or interface while the battery status monitor 34 interprets the voltage data. Generally, as a battery drains, its output voltage wanes. While a freshly charged or new battery puts out a peak voltage very close to its rated value, a drained battery will emit a voltage that is significantly less than its rated value. Naturally, that is why it is necessary to know the rated voltage of the battery before the battery status monitor 34 can make any calculation. Based on the rated output value of the battery 12, and the current operating voltage of the battery 12, the battery status monitor 34 determines the state of charge of the battery.

The battery status monitor 34 at least includes software that compares the current operating voltage of the battery 12 to pre-determined percentage thresholds. For instance, if the current operating voltage is greater than an upper threshold, the battery status monitor 34 may rate the remaining charge of the battery 12 as "good." If the operating voltage is between upper and lower thresholds, the monitor 34 may report the battery status as "low." Finally, if the battery's 12 current voltage is below the lower threshold, the monitor 34 may label it as "critical." In addition, the battery status monitor 34 may be able to report if the state of the battery is unknown, such as if the component 10 leaves the reception range of the receiver 22 for more than a pre-determined number of expected transmissions. The preferred battery status monitor 34 is able to provide a user with more exact information, so the user can more accurately determine whether it is prudent to replace or charge the battery, or to wait and let the component 10 operate longer at its current status.

Figure 3:
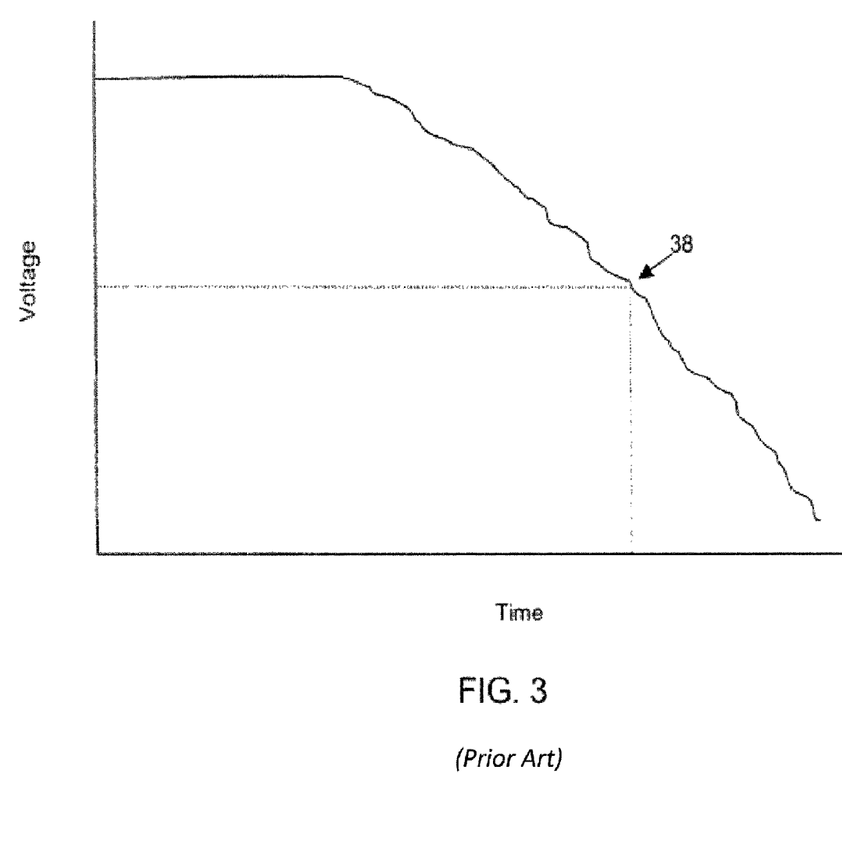
FIG. 3 is a time v. voltage graph of a typical battery voltage decay.

By storing historical voltage readings and usage in a historical memory 36, the battery status monitor 34 can chart a voltage/remaining usage history. That is, for this battery in this device, for the procedures it commonly or is scheduled to perform, the historical data enables the number of remaining procedures on the battery to be projected or, for continuous monitoring operations, the time the battery will run out. Charging or replacement of the battery 12 is indicated by a significant increase or spike in the actual reported operating voltage. As shown in FIG. 3, from actual reported voltage data points, coupled with typical drainage patterns, the battery status monitor 34 can extrapolate an expected battery life curve, and determine an estimated critical point 38 in time where the battery operating voltage will become insufficient to operate the component 10 or perform further procedures completely. In this manner, an estimate of how long the battery 12 will last, and whether and when it would be prudent to replace or charge the battery 12 is made. Common questions a user may ask may be can the battery make it through the weekend? Through the night? Through the next clinical scan? In this manner a user can take the proper steps to make sure that the battery 12 will not die at an inopportune moment.

Additionally, the battery history memory 36 can retain the battery life curves of the battery 12 assuming that it is rechargeable. As the battery 12 grows older and its ability to hold a charge wanes, the expected battery life will grow shorter. Once the battery status monitor 34 compares the battery's 12 ability to hold a charge with a degree of degradation it recommends replacement of the rechargeable battery, rather than just charging it.

Figure 4:
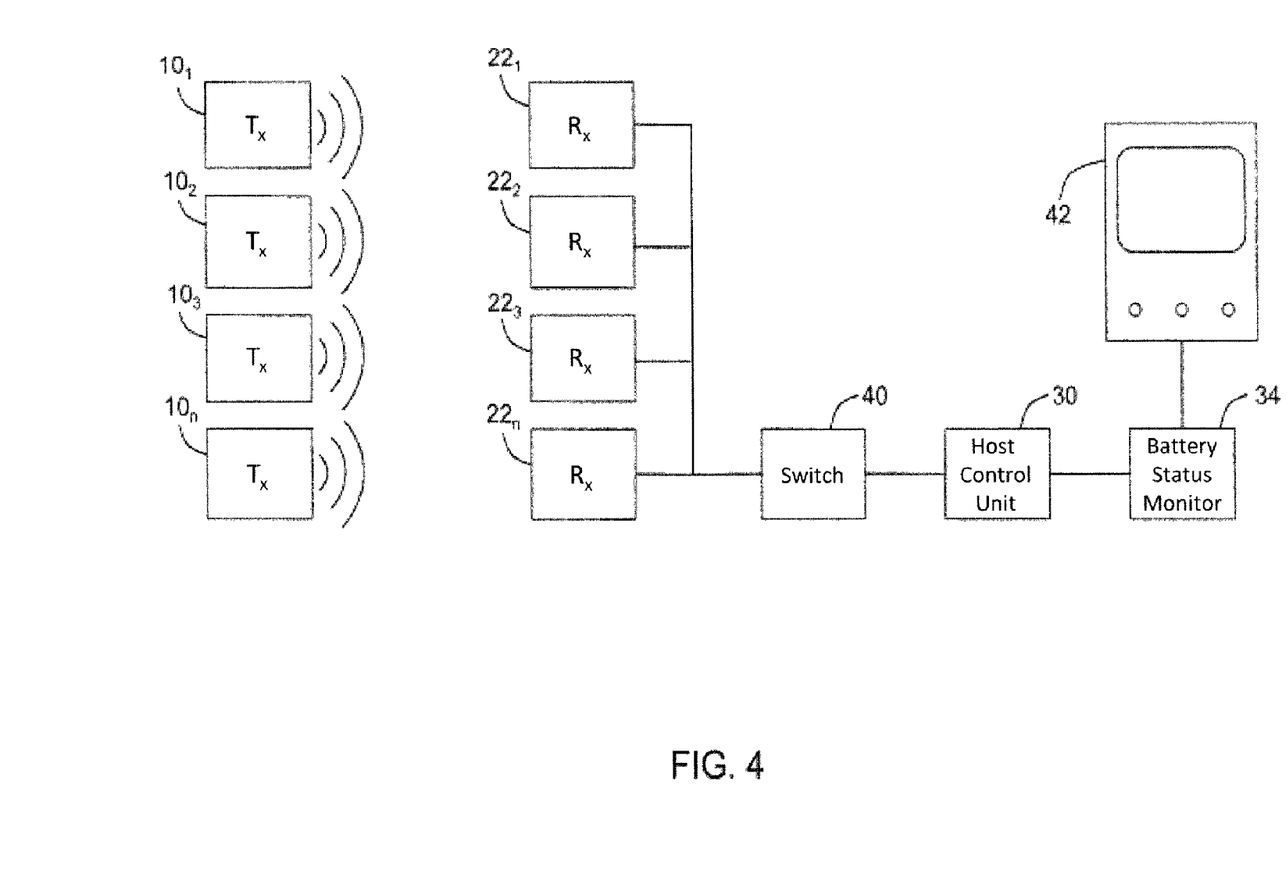
FIG. 4 is an illustration of the battery monitoring system where the components and receivers are in a 1:1 ratio.

In one embodiment, shown in FIG. 4, there are a plurality of components $10_1$-$10_n$ and receivers $22_1$-$22_n$. Although illustrated as a 1:1 correspondence, there can be fewer receivers when the components are networked or are configured such that several can report to a common receiver. Conversely, if a large physical area is monitored with fixed receivers, there can be more receivers than active components. In the illustrated 1:1 correspondence embodiment, each receiver $22_1$-$22_n$ is wired to a common host control unit 30 via a high speed switch 40, or other networking device. In this embodiment a single receiver $22_1$ is responsible for a single component $10_1$. In this embodiment, the receiver $22_1$ may be programmed to attach the ID of the component $10_1$ or its battery for which it is responsible as a rider to the signal. This embodiment may be useful, for example, if a component 10 is meant for use in one room only, such as an MRI receive coil. It may also be useful in a residential setting, such as to monitor the battery life of a respirator.

Figure 5:
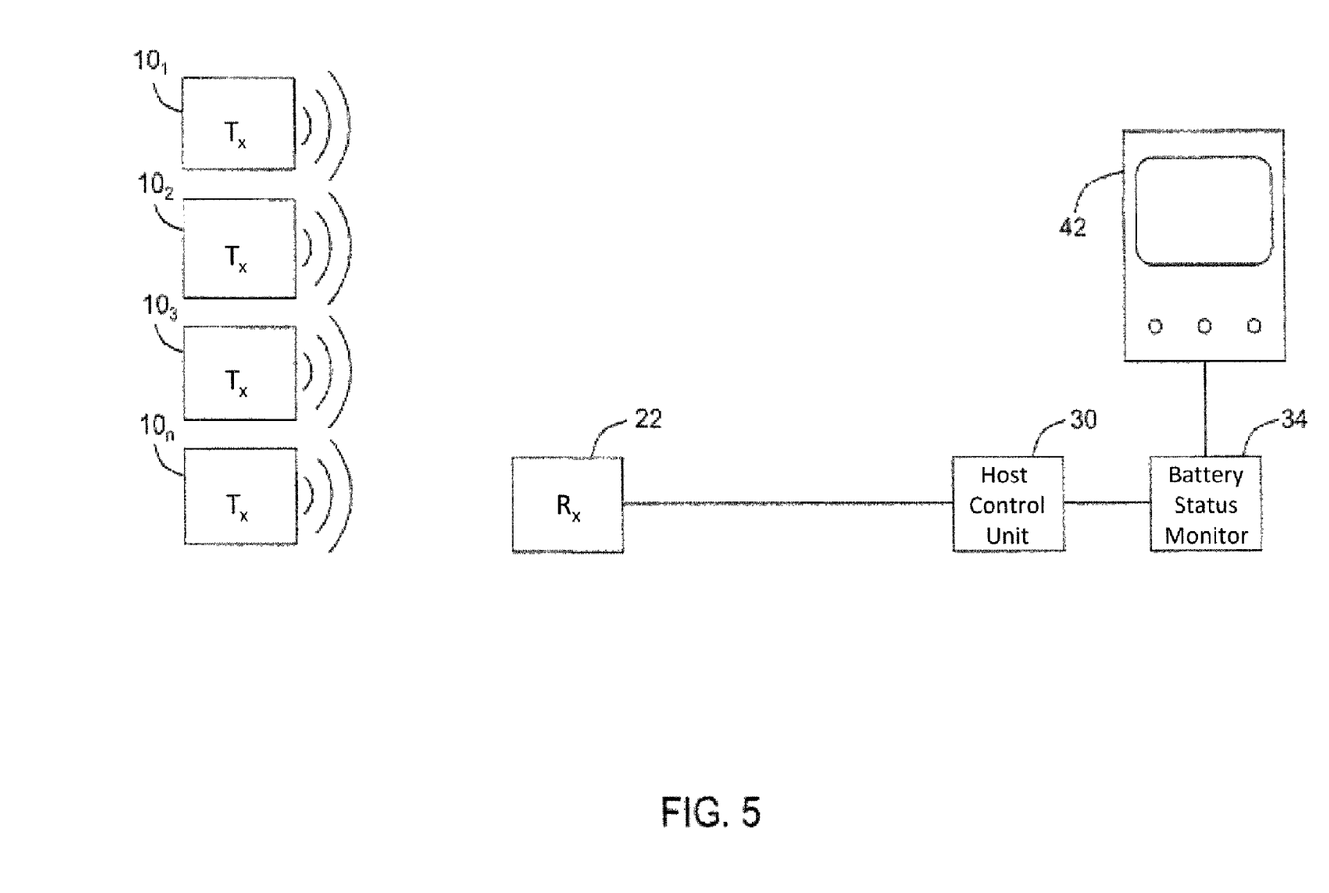
FIG. 5 is an illustration of the battery monitoring system where a single receiver receives signals from multiple components.

In another embodiment, as shown in FIG. 5, shows multiple components $10_1$-$10_n$ that transmit to a common receiver 22. This receiver is connected to the common host control unit 30 and the battery status monitor 34 as in FIG. 1. This embodiment may be useful where multiple devices operate in a common room or travel together as a set.

Figure 6:
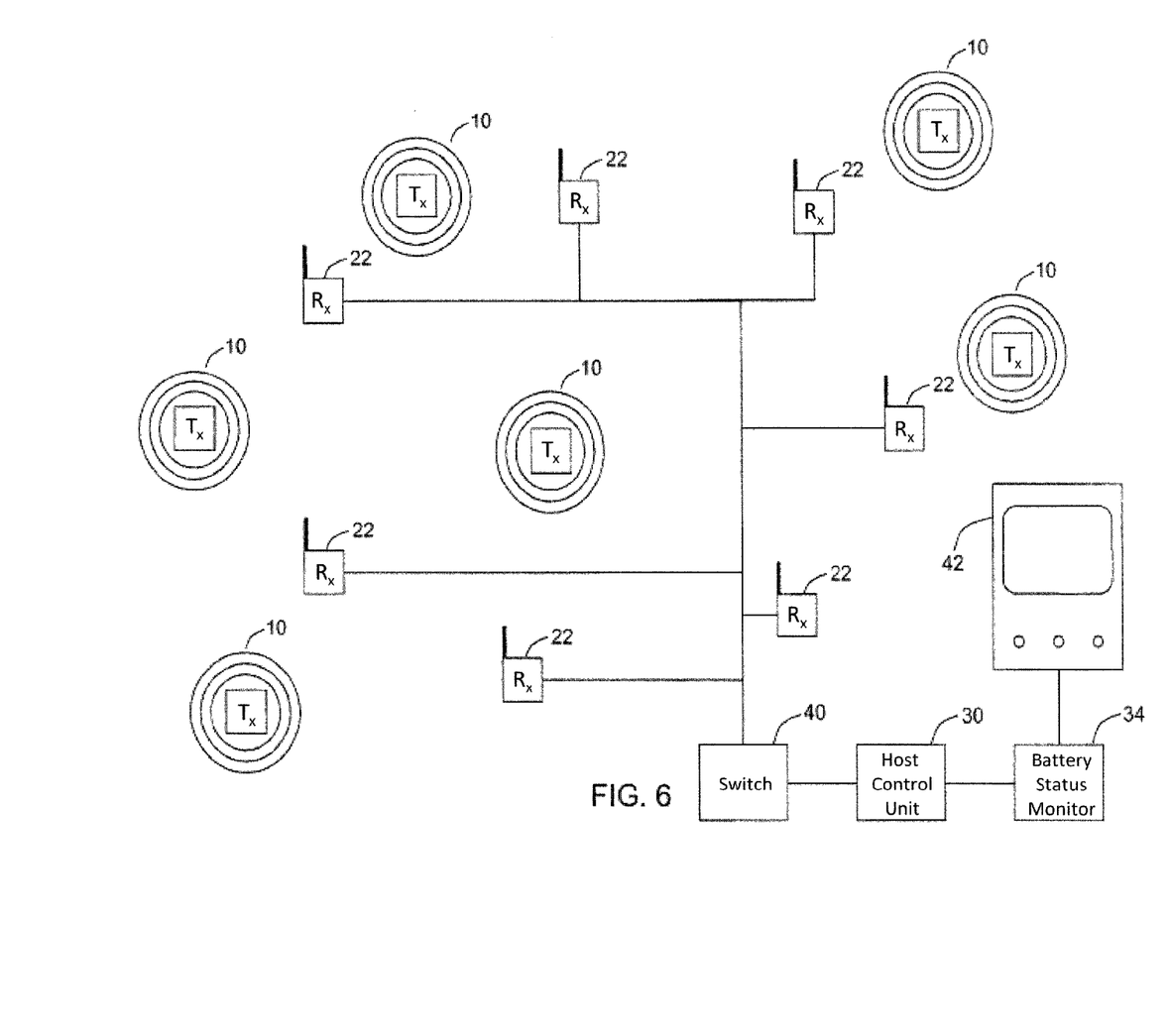
FIG. 6 is an illustration of the battery monitoring system implemented in a wireless hot spot environment.

In another embodiment, as shown in FIG. 6, wireless receivers 22 are distributed around an area with overlapping areas of coverage creating an aggregate wireless "hot spot" where any one of many components 10 can transmit to any of the receivers. For example, in a hospital environment, patients on extended stays are encouraged to get up and move around, if they are able, their IV pumps and stands, physiological condition monitors, medication dosing devices, and the like going with them. Patients might travel all over the floor, or all over the hospital, so a wide area of wireless reception coverage is needed. The components 10 are preferably programmed to transmit identifiers in each signal packet. Should multiple receivers detect the same transmission from the component 10 either the host control unit 30 can reconcile duplicative received transmissions.

In all embodiments, once the battery status monitor 34 has information to convey to the user, that information is displayed on a user interface 42. Preferably, and especially in multiple component embodiments, the component is identified along with its estimated battery life. Preferably, the battery status monitor 34 is a program that runs in the background of a computer's operating system. The user can access the program by clicking an icon, bringing up a list of the active components 10 that the battery status monitor 34 is currently monitoring. When a component is to be associated with a patient, the nurse or technician is shown the remaining battery life of the selected component. Alternately, when a nurse or technician schedules a procedure on the interface, a list of the components with sufficient battery life to perform the procedure is displayed. If a component with insufficient battery life to complete the procedure is selected, a warning can be displayed. Further, when a large number of procedures are scheduled by many nurses or technicians, the host device can match battery requirements with remaining battery life and schedule which component will be assigned to each procedure.

Alternately, battery maintenance may be an assigned task. A nurse's aide or other technician can easily access a list of components and their battery statuses, and see which components should be returned to their chargers, or have their batteries replaced. Alternately the battery life information can be routed to a battery maintenance center. Optionally, an audible or visual alarm may be sounded either at the component location, the host device location, and nurses' station or the like to warn that a component 10 battery 12 is within a preselected threshold of dying.

In an alternate embodiment, the transmitter 20 could instead be a transceiver. The current battery status could then be transmitted back to the component which may affect the activity of the component. For instance, a component with some amount of random access memory (RAM) may receive a message that its battery 12 is critically low. This may trigger the component to enter a state in which it conserves power by continuing only essential functions, such as ensuring that any information stored in RAM will remain intact. If the component is in a network, the low battery signal can transfer some or all or its functions to other network components that have redundant capacity regarding one or more of its functions.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. A medical system, comprising:
    a wireless x-ray detector which generates image data according to received x-rays from an x-ray source, the wireless x-ray detector including:
        a rechargeable battery which powers the wireless x-ray detector,
        a charge level monitor which monitors a charge level of the rechargeable battery and generate corresponding charge level data,
        a transmitter which wirelessly transmits signals carrying the image data and the charge level data from the wireless x-ray detector and the charge level monitor, respectively;
    a host device connected with a receiver which receives the transmitted signals from the wireless x-ray detector, the host device including:
        a data processor which processes the image data received from the wireless x-ray detector, and a battery status monitor which analyzes the received charge level data and determines an estimated remaining battery life of the wireless x-ray detector therefrom.

2. The medical system as set forth in claim 1, further including:
- at least one battery operated functional medical component powered by at least one battery, the at least one battery operated functional component generating functional data and battery charge level data, the at least one battery operated functional medical component including a battery operated EKG sensor, a battery operated pulse sensor, a battery operated blood oxygen sensor, a battery operated blood measure sensor, a battery operated brain wave sensor, a battery operated temperature sensor, a battery operated perfusion pump, a battery operated IV drip controller, a battery operated patient identification tag, a battery operated wrist band, a battery operated respirator, or a battery operated MRI coil; and
- the at least one battery operated functional medical component each including a transmitter which transmits the functional data and the functional medical component battery charge level data wirelessly to the host device.

3. The medical system as set forth in claim 2, wherein the host device further includes:
- a user interface on which a user can view the estimated remaining battery life and the functional data .

4. The medical system as set forth in claim 1, wherein the wireless x-ray detector further includes:
- a voltage charge monitor which monitors an operating voltage of the rechargeable battery.

5. The medical system as set forth in claim 1, wherein the transmitter includes a short range radio frequency transmitter.

6. The medical system as set forth in claim 1, wherein the battery status monitor includes a processor which extrapolates a battery life curve based on the received charge level data from the charge level monitor and typical drainage patterns, determines an estimated critical point in time when the rechargeable battery operating voltage will become insufficient to operate the wireless x-ray detector, and reports an estimated battery life according to the estimated critical point.

7. The medical system as set forth in claim 1, wherein the host device further includes:
- a historical data memory which stores historical data regarding battery discharge rates; and
- wherein the battery status monitor determines discharge rates of the rechargeable battery, and determines the estimated remaining battery life of the rechargeable battery from the determined discharged rates and the historical data.

8. The medical system as set forth in claim 1, further including additional battery powered wireless medical components that communicate with the host device.

9. The medical system as set forth in claim 8, wherein the additional battery powered wireless medical components communicate with additional host devices.

* * * * *